United States Patent [19]

Seymour et al.

[11] 4,324,578
[45] Apr. 13, 1982

[54] METHOD OF PREPARING A COPPER COMPLEX FOR USE AS AN ALGAECIDE

[75] Inventors: Donald E. Seymour, River Hills; Greg A. Seymour, Brown Deer, both of Wis.; Mark J. Jaber, Goldsboro, N.C.

[73] Assignee: Applied Biochemists, Inc., Mequon, Wis.

[21] Appl. No.: 124,098

[22] Filed: Feb. 25, 1980

Related U.S. Application Data

[63] Continuation-in-part of Ser. No. 833,458, Sep. 15, 1977, abandoned, which is a continuation of Ser. No. 100,335, Jun. 8, 1976, abandoned.

[51] Int. Cl.³ .................... A01N 31/02; A01N 55/02; A01N 59/20
[52] U.S. Cl. .......................... 71/67; 71/97; 71/66
[58] Field of Search ................. 71/67, 66, 97

[56] References Cited

U.S. PATENT DOCUMENTS

| | | | |
|---|---|---|---|
| 2,446,682 | 8/1948 | Whitner | 8/54.2 |
| 2,446,682 | 8/1948 | Whitner | 260/438.1 |
| 2,551,446 | 5/1951 | Marks | 71/67 |
| 2,734,028 | 2/1956 | Domogalla | 71/67 |
| 2,878,155 | 3/1959 | Cruickshank | 71/67 |
| 2,894,905 | 7/1959 | Bernard | 71/67 |
| 3,591,513 | 7/1971 | Tate | 71/67 |
| 3,634,061 | 1/1972 | Geiger et al. | 71/67 |
| 3,716,351 | 2/1973 | Kunkel et al. | 71/67 |
| 3,792,084 | 2/1974 | Quinlan | 71/67 |
| 3,905,797 | 9/1975 | Kunkel et al. | 71/67 |
| 3,930,834 | 1/1976 | Schulteis et al. | 71/66 |
| 4,030,907 | 6/1977 | McNall | 71/67 |
| 4,075,326 | 2/1978 | Kuyama et al. | 71/67 |

FOREIGN PATENT DOCUMENTS

| | | | |
|---|---|---|---|
| 2506431 | 9/1975 | Fed. Rep. of Germany | 71/67 |
| 2243643 | 4/1975 | France | 71/67 |
| 1479052 | 7/1977 | United Kingdom | 71/67 |

*Primary Examiner*—Glennon H. Hollrah
*Attorney, Agent, or Firm*—Andrus, Sceales, Starke & Sawall

[57] ABSTRACT

A method of preparing a copper complex to be used in eliminating the growth of aquatic or marine plant life, such as algae. The copper complex is formed by reacting finely divided water-insoluble copper carbonate with the combination of monoethanolamine and triethanolamine. The copper compound is completely solubilized and complexed by the combination to provide a copper complex having improved stability and containing an increased amount of elemental copper as compared to copper complexes formed by prior methods, thereby making the complex more effective as an algaecide.

9 Claims, No Drawings

METHOD OF PREPARING A COPPER COMPLEX FOR USE AS AN ALGAECIDE

This application is a continuation-in-part of application Ser. No. 833,458, filed Sept. 15, 1977, and now abandoned which in turn is a continuation of application Ser. No. 100,335, filed June 8, 1976, and now abandoned.

Copper ions are known to be effective against the growth of algae. In the past, water-soluble copper compounds, such as copper sulfate, have been used extensively as algaecides. Copper ions released by copper sulfate when added to water, react with carbonates or bicarbonates found in water to produce insoluble copper compounds which precipitate and cause turbidity or cloudiness in the treated water. If excessive amounts of insoluble copper compounds settle out, the compounds can form a sludge or deposit, which in the case of a lake or stream, may tend to destroy the fish life or zooplankton which is essential as fish food.

To overcome the problems associated with the use of copper sulfate, a complex formed by the reaction of copper sulfate and an alkanolamine, as disclosed in U.S. Pat. No. 2,724,028, has been used and has achieved wide success as an algaecide. A complex of this type has the ability to maintain the copper ions in solution, even when the algaecide is added to alkaline water containing high proportions of carbonates or bicarbonates, as well as soft water situations.

It has been found that a copper alkanolamine complex of the type disclosed in U.S. Pat. No. 2,734,028 tends to decompose when subjected to sunlight and/or warm temperatures, resulting in a precipitation of copper, thereby removing the toxic copper ions from solution and decreasing the effectiveness of the complex as an algaecide. As a further disadvantage, a copper complex prepared from the copper sulfate is highly corrosive, thereby presenting problems in handling, shipping and storage of the concentrate.

The presence of the sulfate ions provides a further disadvantage in that when the concentrate is added to the water to be treated in the recommended dosage, the sulfate content can be conductive to diatom blooms.

To avoid the problems associated with the use of copper sulfate, a copper complex has been prepared using water-insoluble copper compounds, as disclosed in U.S. Pat. No. 3,930,834. In this latter patent, the complex is formed by initially reacting an insoluble copper compound with an acid in aqueous solution to dissociate the copper ions, and thereafter chelating the released copper ions to form the copper complex. The complex formed by the method of U.S. Pat. No. 3,930,834 has improved stability to both heat and light as compared with a copper complex formed from copper sulfate and enables a larger proportion of elemental copper to be put into solution. However, the use of the acid in the process substantially increases the material cost, as well as introducing safety problems in the handling and storage of the acid.

SUMMARY OF THE INVENTION

The invention relates to an improved method of preparing a copper complex to be used as an algaecide. In accordance with the invention, the copper complex is produced by mixing powdered or finely divided, water insoluble copper carbonate with the combination of monoethanolamine and triethanolamine.

Copper carbonate, commercially available as basic copper carbonate, is the least expensive of the most readily available water insoluble copper compound, because of this, it is advantageous to use copper carbonate as the copper source in forming a copper complex for use as an algaecide. However, solubilization and chelation of copper carbonate is extremely difficult in the absence of an acid, particularly at higher copper concentrations. The most common chelating agents, such as triethanolamine, cannot, at any molar ratio, totally put high concentrations of copper carbonate into solution as a copper complex.

The invention is based on the discovery that high concentrations of copper carbonate can be totally solubilized and chelated to form a water soluble copper complex through use of the combination of monoethanolamine and triethanolamine. The monoethanolamine allows for total solubilization of the copper carbonate and the addition of triethanolamine results in an unusually stable copper complex. No filtration or centrifugation is required to remove undissolved copper carbonate or precipitated copper compounds and this attests to the unusual stability of the chelated copper solution.

As an unusual and unexpected advantage, the solubilization of the copper carbonate through the method of the invention eliminates the copious foaming that is normally associated with the acid solubilization of copper carbonate. For some unexplained reason, the dissociated carbonate ions are retained in solution rather than being evolved as carbon dioxide gas.

Retaining the carbonate ions in solution provides a two-fold benefit. First, the pH of the finished product is maintained within an acceptable range which eliminates the necessity of adjusting the pH through the addition of an acid. Second, the lack of generation of carbon dioxide gas eliminates a portential health hazard and reduces costs by negating the necessity for special ventilation equipment.

By complexing or chelating the insoluble copper carbonate, without the use of acids, the process substantially reduces costs, as well as minimizing handling and safety problems in the production process. As the complex can be formed without the use of sulfates, the concentrate is less corrosive than a concentrate formed through use of copper sulfate. The potential toxicity to fish and zooplankton which can occur in the presence of sulfates is also eliminated.

The complex formed by the method of the invention also has improved stability to both heat and light with the result that the copper will not precipitate from the solution over extended periods of exposure to high temperatures and/or sunlight. This results in a longer shelf-life and greatly simplifies storage and transportation requirements.

The complex formed by the method of the invention is particularly effective as an algaecide due to the fact that the complex can contain up to about 13% by weight of elemental copper.

DESCRIPTION OF THE PREFERRED EMBODIMENT

The copper complex of the invention is produced by reacting finely divided, or powdered, water insoluble copper carbonate with the combination of monoethanolamine and triethanolamine.

The monoethanolamine is used in a molar ratio slightly in excess of 2:1 with respect to the copper concentration and preferably in the molar ratio of 2.1:1 to 2.7:1, while the triethanolamine is employed in a molar concentration slightly in excess of 1:1 with respect to the copper concentration and preferably in the molar ratio of about 1.1:1.

The monoethanolamine and triethanolamine are normally used in aqueous solution. The concentration of the solution, however, is not critical and can vary within wide limits.

No special techniques are required for preparing the complex. The complex is prepared by adding the powdered copper carbonate to the combination of monoethanolamine and triethanolamine with gentle mixing or stirring. Elevated temperatures are not required, although heating can accelerate the solubilization and chelation. As an alternate procedure, the copper carbonate can be initially mixed with the monoethanolamine to achieve solubilization and subsequently the triethanolamine can be added to the solution.

Forming a copper complex from copper carbonate by the method disclosed in U.S. Pat. No. 3,930,834, in which the copper carbonate is initially reacted with an acid in aqueous solution to dissociate the copper ions and thereafter the released copper ions are chelated to form the complex, produces a copious generation of carbon dioxide gas. The generation of the carbon dioxide gas provides a potential health hazard and requires special ventilating equipment.

As an unusual and unexpected result, the solubilization of the copper carbonate through the method of the invention eliminates the evolution of carbon dioxide and the resulting foaming that is normally associated with the acid solubilization of copper carbonate. For some reason not fully understood, the dissociated carbonate ions are retained in solution, rather than being evolved as carbon dioxide gas. The lack of generation of carbon dioxide gas eliminates the potential health hazard and simplifies the ventilation equipment required for the processing.

Retaining the carbonate ions in solution also provides a second advantage in that the pH of the final product is maintained within an acceptable range without the necessity of adjusting the pH downward through the addition of an acidic component.

The copper complex prepared in accordance with the invention has a pH in the range of 8.0 to 11.0 and normally within the range of about 9.5 to 10.3. The use of copper carbonate, as the source of copper, results in the pH of the complex being substantially lower than the pH of complexes formed from most other water insoluble copper compounds, i.e. copper hydroxide, which normally have pH values of 11.0 or higher before adjustment with acids. With a pH of 10.5 or above, the complex cannot satisfactorily be mixed with common aquatic herbicides because of coagulation and precipitation of the herbicide-chelated copper mixture.

The process of the invention, by retaining the carbonate ions in solution, enables the pH of the final complex to fall within an acceptable range without the necessity of adjusting the pH through the addition of an acid. By eliminating the acid adjustment of pH, the time and cost of the processing is reduced, as well as eliminating the potential safety hazards associated with the storage, handling and use of the acid.

The combination of monoethanolamine and triethanolamine is particularly effective in totally solubilizing and chelating the copper compound, because the chelation occurs in a relatively short period of time and the resulting copper complex is particularly stable to hydrolysis.

It is believed that the monoethanolamine effects the total solubilization of the copper carbonat?, and the triethanolamine, along with the monoethanolamine at least to a minor degree, provides the chelation to obtain an unusually stable copper complex. At high copper concentration of over 7% the entire solubilization and chelation will occur within a period of less than 90 minutes. With this time period, the total copper concentration is converted to the complex so that the finished product does not require filtration and/or centrifugation to remove undissolved copper carbonate or precipitated copper compounds.

The copper complex can contain up to about 13% by weight of elemental copper, and preferably 7% to 9%. Lower percentages of elemental copper can be obtained by direct formulation or by simple water dilution of the more concentrated product. The high concentration of elemental copper increases the effectiveness of the solution as an algaecide. As the copper is maintained in solution as the complex, the entire toxic effect of the copper as an algaecide is realized, thereby achieving a saving in the amount of copper and in total algaecide use, with the result being a saving in total cost per acre treated.

The solution containing the copper complex is normally stored, handled and transported as a concentrate containing about 50% to 80% by weight of the complex. The concentrated solution is normally diluted at the time of use in the ratio of 5 to 50 parts of water for each part of concentrated solution. The diluted solution is applied to the body of water so that the body of water contains from about 0.20 to 20.0 ppm by weight of elemental copper.

The algaecidal composition is effective against most common forms of algae, including filamentous algae, such as Cladophora and Spirogyral planktonic algae such as Anacystis and Anabaena; chara algae such as *Chara vulgaris* and Nitella; and swimming pool algae such as Oscillatoria, Phormidium and Chlorella.

The copper complex as formed by the invention has also been shown to be effective as a herbicide against certain vascular aquatic plants such as *Hydrilla verticillata* and *Potamogeton crispus*.

PREPARATION OF THE COPPER COMPLEX

The following examples illustrate the preparation of the copper complex of the invention.

EXAMPLE I 17 grams of powdered copper carbonate were added to 20 grams of monoethanolamine, 26 grams of triethanolamine and 38 grams of water with gentle mixing at room temperature. Within a period of 3 to 4 minutes a dark blue solution resulted, evidencing the formation of the chelated copper. The resulting solution contained 9.4% by weight of elemental copper and had a pH of 10.0. A clear solution was obtained with no remaining undissolved copper carbonate, no precipitate and no suspended particulate material in evidence.

EXAMPLE II 825 pounds of powdered copper carbonate (55.2% copper: w/w) were added to 230 gallons of water and 120 gallons of monoethanolamine. The batch was mixed at high speed with medium shear for a 30 minute period. 136 gallons of triethanolamine were added and mixing was continued for an additional 60 minutes. The resulting 500 gallon clear dark blue solution was free of particulate matter, had a pH of 9.9 and contained 9% (w/w) of elemental copper as determined by instrumentation.

EXAMPLE III 660 pounds of powder copper carbonate (55.2% copper: w/w) were added to 277 gallons of water, 96 gallons of monoethanolamine and 109 gallons of triethanolamine. The batch was mixed at high speed with medium shear for a 90 minute period. The resulting 500 gallon clear dark blue solution was free of particulate matter, had a pH of 9.6 and contained 7.4% (w/w) of elemental copper as determined by instrumentation.

HEAT STABILITY TEST

Samples of the copper complex prepared in accordance with Example I were stored in glass containers and subjected to a temperature of 104° F. for a period of 4 months. After this period there was no visible deposit or precipitation of copper in the containers and no measurable loss of copper from the solution as determined by instrumentation.

A second series of samples were prepared using copper sulfate to produce the complex, as disclosed in U.S. Pat. No. 2,734,028. In preparing these samples, 100 ml of triethanolamine was added to 90 ml of water and enough copper sulfate was dissolved in the solution to produce a 7.1% by weight solution of elemental copper. Samples of the concentrated solution containing the complex produced through use of copper sulfate were stored in glass containers and subjected to a temperature of 104° F. After 4 months, a plating of copper was noted on the walls of the containers, and the solutions lost in the range of 0.50% to 0.67% copper from solution as determined by instrumentation.

The heat stability test indicated the improvement in heat stability achieved by the copper complex prepared by the method of the invention, as compared to that prepared from copper sulfate.

LIGHT STABILITY TEST

A series of samples of the concentrated solution of the copper complex prepared in accordance with Example I were stored in sealed glass containers and exposed to both natural sunlight and artificial light for a period of 4 months. After this period, there was no visible deposit or precipitation in the containers, as well as no significant measurable loss of copper from solution as measured by instrumentation designed for copper assay measurements.

Similar samples of the concentrated solution of the complex produced from copper sulfate, prepared by the method outlined above, were similarly stored in glass containers and subjected to both natural sunlight and artificial light for a period of 4 months. After this period, a plating of copper was visible on the container walls and instrumentation indicated that the solution lost from 0.50% to 0.75% by weight of elemental copper.

This test indicates the substantial improvement in stability to light of the complex produced by the method of the invention, as compared to that produced from copper sulfate.

ALGAECIDAL EFFECTIVENESS TEST

A pond of approximately 1 acre in area and having an average depth of 5 feet and having a heavy infestation of Cladaphora and Spirogyra strains of algae, was treated with the copper complex prepared in accordance with Example I at a rate of 0.6 gal./acre to provide a copper concentration of approximately 0.2 ppm. After a period of 3 days all traces of the algae has disappeared from the water surface.

Various modes of carrying out the invention are contemplated as being within the scope of the following claims particularly pointing out and distinctly claiming the subject matter which is regarded as the invention.

We claim:

1. An algaecide comprising an aqueous solution containing an algaecidal effective amount of a water soluble copper complex produced by mixing finely divided water insoluble copper carbonate with the combination of monoethanolamine and triethanolamine, said monoethanolamine being present in a molar ratio slightly in excess of 2:1 with respect to the copper concentration and the triethanolamine being present in a molar ratio slightly in excess of 1:1 with respect to the copper concentration, said combination acting to completely solubilize and chelate the copper carbonate to form the complex, said aqueous solution being free of acids.

2. The algaecide of claim 1, wherein the solution contains at least 7% by weight of elemental copper.

3. The algaecide of claim 1, wherein the solution has a pH in the range of 8.0 to 11.0.

4. A method of controlling the growth of algae, comprising the steps of contacting algae in a body of water with an algaecidal effective amount of a copper complex produced by reacting finely divided water insoluble copper carbonate with the combination of monoethanolamine and triethanolamine, said monoethanolamine being present in a molar ratio slightly in excess of 2:1 with respect to the copper concentration and the triethanolamine being present in a molar ratio slightly in excess of 1:1 with respect to the copper concentration, said combination acting to completely solubilize and chelate the copper carbonate to form the complex, said aqueous solution being free of acids.

5. A method of preparing an algaecide, comprising the steps of contacting finely divided water insoluble copper carbonate with a sufficient quantity of monoethanolamine to solubilize the copper carbonate, and thereafter contacting the solubilized copper carbonate with a sufficient quantity of triethanolamine to chelate the solubilized copper and provide a copper complex.

6. The method of claim 5, and including the step of maintaining a molar ratio of monoethanolamine to copper slightly in excess of 2:1 and maintaining a molar ratio of triethanolamine to copper slightly in excess of 1:1.

7. A method of preparing an algaecide, comprising the steps of mixing powdered copper carbonate with an aqueous solution of monoethanolamine, maintaining a molar ratio of monoethanolamine to copper in said solution slightly in excess of 2:1 to completely solubilize all of the copper carbonate and retain the carbonate ions in solution, contacting the solubilized copper carbonate with triethanolamine, maintaining a molar ratio of triethanolamine to copper slightly in excess of 1:1 to chelate the copper ions and provide a copper complex solution, and packaging the copper complex solution without adjustment of the pH.

8. The method of claim 7, wherein the monoethanolamine and triethanolamine are simultaneously mixed with the copper carbonate.

9. The method of claim 7, wherein the monoethanolamine is initially mixed with the copper carbonate and thereafter the triethanolamine is added to the solution.

* * * * *